(12) United States Patent
Okerlund et al.

(10) Patent No.: US 6,526,117 B1
(45) Date of Patent: Feb. 25, 2003

(54) METHOD AND APPARATUS TO MINIMIZE PHASE MISREGISTRATION ARTIFACTS IN GATED CT IMAGES

(75) Inventors: Darin R. Okerlund, Muskego, WI (US); Sankar V. Srinivas, Milwaukee, WI (US); Jerome F. Knoplioch, Nueilly sur Seine (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/044,672

(22) Filed: Nov. 9, 2001

(51) Int. Cl.[7] ................................................. A61B 6/00
(52) U.S. Cl. ................................ 378/8; 378/4; 382/131
(58) Field of Search ................................ 378/8, 201, 4, 378/15; 382/131

(56) References Cited

U.S. PATENT DOCUMENTS 4,868,747 A  * 9/1989 Mori et al. ............. 364/413.18
6,154,516 A  * 11/2000 Heuscher et al. .............. 378/15
6,252,924 B1 * 6/2001 Davantes et al. .............. 378/8
6,272,200 B1 * 8/2001 Pan et al. ...................... 378/15

FOREIGN PATENT DOCUMENTS

| JP | 2000-230611 | 8/2000 |
| JP | 2000-234656 | 8/2000 |

* cited by examiner

Primary Examiner—Drew A. Dunn
Assistant Examiner—Irakli Kiknadze
(74) Attorney, Agent, or Firm—Quarles & Brady, LLP; Carl Horton

(57) ABSTRACT

A method and apparatus for generating an optimally registered working set of two-dimensional CT images in a gated CT system, the method including, where an acquisition period is divided into sequential acquisition phases, obtaining CT image data for separate phase ranges during each acquisition phase, generating phase image sets including 2D images for each phase range and selecting one phase range image set corresponding to each acquisition phase to generate a working image set where the selected phase range image sets are optimally aligned.

21 Claims, 6 Drawing Sheets

METHOD AND APPARATUS TO MINIMIZE PHASE MISREGISTRATION ARTIFACTS IN GATED CT IMAGES

STATEMENT REGARDING FEDERALLY SPONSORED RESEARCH

Not applicable.

CROSS-REFERENCE TO RELATED APPLICATIONS

Not applicable.

BACKGROUND OF THE INVENTION

The field of the invention is gated computerized tomography (CT) imaging and more specifically methods and apparatus that reduce the amount of misalignment between parallel two dimensional images in a working CT image set.

Many different types of medical imaging systems have been developed that are used for different purposes. Perhaps the most common type of imaging system category includes X-ray systems wherein radiation is directed across a portion of a patient to be imaged and toward a detector panel. An exemplary X-ray detector panel includes a CsI scintillator coupled with an amorphous silicon array. With radiation directed toward a region of a patient to be images (i.e., a region of interest), the region of interest blocks some of the radiation and some of the radiation passes through the region and is collected by the panel. The amount of radiation that passes through the region along the trajectory of a given radiation ray depends upon the type of tissue along the trajectory. Thus, a tumor may block more radiation than flesh and bone may block more radiation than a tumor and so on. Hence X-ray system can be used to collect a "projection" through a patient.

While useful, simple X-ray systems have many limitations. One important limitation to X-ray imaging systems is that such systems, as described above, only provide side projections through a region and cannot be used to generate other useful images such as "slice" images (i.e., images perpendicular to projection images) through a region of interest. For instance, an exemplary useful slice image may include a slice image through a patient's heart.

Another type of imaging system that is useful in generating slice images is generally referred to as a computerized tomography (CT) system. An exemplary CT system includes a radiation source and a radiation detector mounted on opposite sides of an imaging area where the imaging area is centered along a translation or Z-axis. The source generates radiation that is collimated into a beam including a plurality of radiation rays directed along trajectories generally across the imaging area. A line detector may be positioned perpendicular to the Z-axis to collect slice image data during a data acquisition period.

During an acquisition period a region of interest is positioned within the imaging area and, with the radiation source turned on, the region of interest blocks some of the radiation and some of the radiation passes through the region and is collected by the line detector. As in X-ray systems, the amount of radiation that passes through the region of interest along the trajectory of a given radiation ray is dependent upon the type of tissue along the trajectory. In CT systems the source and line detector are rotated about the region of interest within a rotation plane through the region of interest so that radiation "projections" can be collected for a large number of angles about the region. By combining the projections corresponding to a slice through the region of interest using a filtering and back projecting technique, a two-dimensional tomographic or axial image (i.e., a slice image) of the slice is generated.

While some diagnostic techniques only require one or a small number of slice images, many techniques require a large number of parallel CT slice images. For example, some techniques require examination of many parallel images to identify where an arterial blockage begins and ends and the nature of the blockage there between. As another example, many techniques reformat two dimensional data into, in effect, three dimensional volumetric images, that can be sliced and diced in several different directions so that various image planes can be employed. For instance, where two dimensional data is acquired for transverse or cross sectional slices through a three dimensional region of interest (e.g., through a patient's torso), the data may be reformatted to generate sagital (i.e., the side plane passing through the long axis of the body) or coronal (i.e., the frontal plane passing through the long axis of the body) images through the region of interest.

In order to generate several slice images rapidly, CT detectors are typically configured having several parallel detector rows such that, during a single rotation about the imaging area, each detector row collects data that can subsequently be used to generate a separate CT slice image.

While increasing the number of detector rows reduces acquisition time, detector elements are relatively expensive and thus more rows translates into a more costly overall system. As a balance between cost and speed, most multi-row detectors include less than 10 detector rows. Hereinafter it will be assumed that an exemplary detector includes eight detector rows.

Where a detector includes eight rows and more than eight slice images are required, several different acquisition periods are typically used to acquire the necessary slice image data. For instance, assume that 80 slice images (an admittedly small number but sufficient for exemplary purposes) through a ROI are required. In this case, the ROI may be divided into ten separate sub-volumes, each of the ten sub-volumes corresponding to a separate eight of the 80 required slice images. Thereafter, ten separate acquisition periods may be used to collect the sets of slice image data corresponding to the ten sub-volumes, data corresponding to eight separate slice images collected during each of the ten separate acquisition periods.

It has been found that, for large volumes or ROIs, data necessary to generate many parallel thin slice images can be acquired most rapidly by helically collecting the data. To this end, while the source and detector are rotated about the imaging area, a patient bed is translated there through so that the radiation fan beam sweeps a helical path through the ROI. After helical data is collected, the data is converted to slice image data by any of several different weighting and filtering processes and thereafter the slice image data is backprojected to form the viewable image.

In the case of helically acquired and stored raw data, the data can be used to construct virtually any number of slice images through a corresponding ROI. For instance, despite using a detector having eight rows of elements to collect helical data, the data may be processed to generate 16, 20, 500 or even thousands of separate slice images or, indeed, may be interpolated to generate a 3-D volumetric image, if desired.

In most imaging systems that generate still images, it is important that, to the extent possible, during data acquisition, the structure being imaged remain completely still. Even slight structure movement during acquisition can cause image artifacts in, and substantially reduce the diagnostic value of, resulting images. For this reason, during acquisition periods, patients are typically instructed to maintain the region of interest within the imaging area as still as possible by, for instance, holding the patient's breadth.

Despite a patient's attempts to control movement, certain anatomical structures cannot be held still and continue movement during acquisition periods. For instance, a patient's heart beats continually during data acquisition cycles and the beating movement complicates the process of acquiring diagnostic quality data.

In the case of the heart, fortunately, the beating cycle is repetitive and there are certain cycle phases during which the heart muscle is relatively at rest. As well known in the art, during a diastolic phase of the beating cycle when the heart is filling with blood, the heart is relatively at rest and movement is minimal. Thus, by restricting data acquisition periods to the diastolic phases of the heart beating cycle, relatively movement-free data can be acquired and used to generate CT slice images.

To this end, the industry has developed cardiac gated CT imaging systems. These systems generally take two different forms including shoot and move gating scans and retrogating reconstructions. In the case of shoot and move scans, an electrocardiogram (EKG) system is used to monitor heart beating phase and to gate the acquisition of data so that data is only acquired during specific phases of the heart beating cycle (e.g., systolic, diastolic, etc.) Thereafter the data is used to generate slice images in a conventional manner. In the case of retro-gating reconstruction, a full set of helical data is acquired and stored along with corresponding EKG signals. Thereafter, a heart cycle phase range is selected which indicates a range of the cycle for which images should be generated and an image reconstructor retrieves the helical data sub-set corresponding to the phase range from each heart cycle and generates the required images.

In addition to minimizing movement related image artifacts, each of the gating processes (i.e., prospective and retrospective) is also meant to reduce misregistration between sets of images that are generated using data corresponding to different sub-volumes of a region of interest. For instance, in the case above where a region is divided into ten separate sub-volumes and data for each sub-volume is collected during a separate acquisition period, if data for two consecutive sub-volumes were collected during different heart beating phase, resulting images would likely be misaligned. Thus, by collecting data for all sub-volumes during similar heart beating phases, misalignment is substantially reduced. In the cases of axially acquired data and helically acquired data this means restricting data to a specified phase range within each heart beating cycle. For instance, the acquired period may be between 70% and 80% of the total heart beating cycle where the cycle begins and ends at peak cycle amplitudes.

Hereinafter the phrase "phase location" will be used to refer to as a phase point within a heart cycle and the phrase "phase range" will be used to refer to a range that is centered on a corresponding phase location.

Unfortunately, despite cardiac gating efforts, it has been recognized that mis-registration or misalignment of sub-volume images can still occur for several reasons. First, as known in the industry, EKG signals provide only an indirect way to measure heart motion and therefore cannot be used to precisely identify identical phase locations within a heart beating cycle. Second, it is known that, while generally periodic, the heart muscle may not go through precisely the same motions during consecutive heart cycles so that, even if precise phase locations could be identified within a heart beating cycle, those locations may not correspond to a similarly positioned heart. Third, in the case of high heart rates (i.e., a child's heart) the gating system may have inadequate temporal resolution to facilitate proper gating. These gating problems are further exacerbated when attempting to generate images including coronary arteries as segments of a given artery may be at rest at somewhat different phase locations within consecutive heart beating cycles.

Gating related phase mis-registrations can be quite apparent in ventricle walls when viewing an image dataset corresponding to a multi-planar reformat rendering from a sagital or coronal perspective. Similarly, the mis-registrations are apparent in the coronary arteries when viewing an image dataset with a curved reformat rendering.

SUMMARY OF THE INVENTION

It has been recognized that when gated CT techniques are employed to collect image data corresponding to adjacent ROI sub-volumes during sequential acquisition phases, where each acquisition phase is further sub-divided into shorter phase ranges, often image sets corresponding to the different phase ranges within sequential acquisition phase align better than image sets corresponding to the same phase ranges within sequential acquisition phases. For example, assuming adjacent first and second sub-volumes corresponding to first and second sets of eight slice images and that data corresponding to the first and second sub-volumes is to be collected during the diastolic phases of first and second heart beating cycles, respectively. In this case, each of the first and second diastolic phases may be divided into beginning and ending phase ranges including first and second halves of the first and second diastolic phases, respectively.

Also, assume that during the first diastolic phase two sets of image data for the first sub-volume (i.e., for the eight slices of the first sub-volume) are obtained, a first set obtained during the beginning phase range and a second set obtained during the ending phase range. Similarly, assume that during the second diastolic phase two sets of image data for the second sub-volume (i.e., for the seven slices of the second sub-volume) are obtained, a first set obtained during the beginning phase range and a second set obtained during the ending phase range. Even though the beginning phase range data sets correspond to similar phase ranges of the heart beating cycle, it has been found that images generated using the beginning phase range data sets are often characterized by greater mis-registration than images generated using the beginning phase range data set from the first diastolic phase and the ending phase range data set from the second diastolic phase.

Thus, it has been recognized that where data is collected for each sub-volume of a ROI during separate diastolic phases, instead of obtaining a single data set corresponding to each diastolic phase, the diastolic phase can be divided into several phase ranges and a separate sub-volume data set can be obtained for each phase range and thereafter, during post acquisition processing, image sets corresponding to the different phase ranges can be compared and the sets that align or register most accurately can be combined into a working image set for further diagnostic purposes. While the example above where each diastolic phase is divided into beginning and ending phase ranges facilitates better results than systems that do not divide the diastolic phase, alignment is generally further enhanced as the number of diastolic phase divisions are increased. For instance, generally, dividing each diastolic phase into five phases ranges yields better results than dividing each diastolic phase into two phase ranges.

Throughout this specification, while some of the examples are described in the context of either a prospective gating method or a retrospective gating method, it should be understood that the present invention is useable with in prospective or retrospective methods and processors and should not be limited to one or the other. It should suffice to say that where an example is taught in the context of one or the other types of systems, the type of system not literally taught has only been omitted in the interest of simplifying this explanation and not to limit the invention in any way.

It should also be noted that the present invention is also useful in the case of advanced multi-sector reconstruction algorithms to improve temporal imaging resolution. These algorithms and how the present invention would be used therewith should be obvious to one of ordinary skill in the art in light of the specification which follows.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DESCRIPTION OF THE PREFERRED EMBODIMENT

A. Hardware

Figure 1:
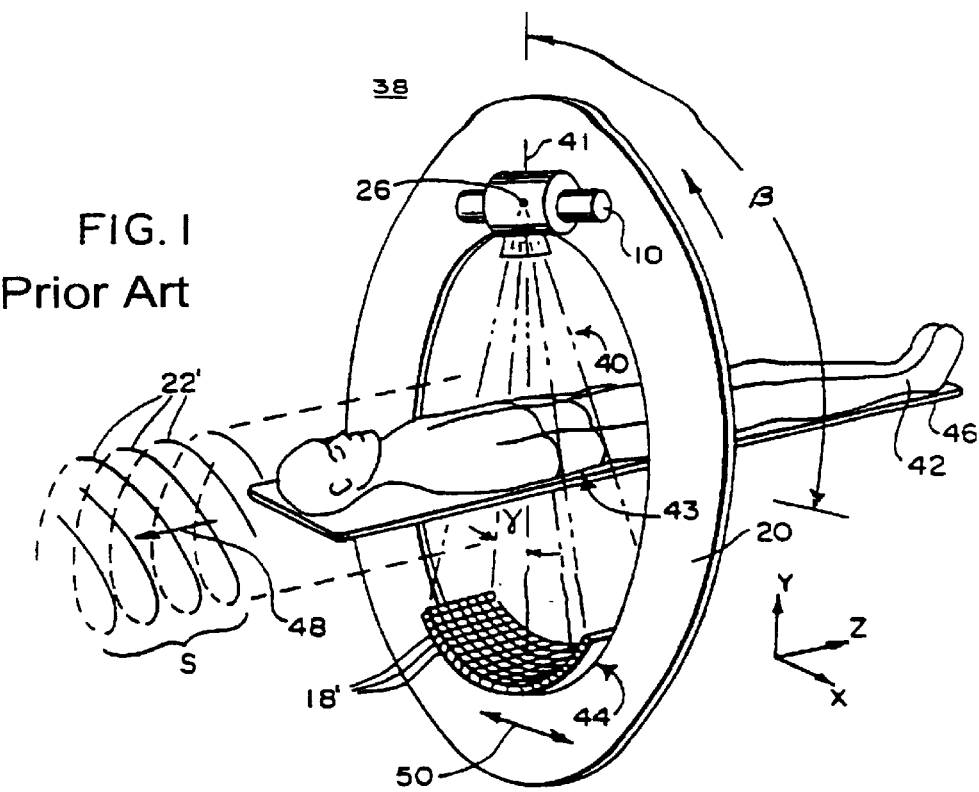
FIG. 1 is a perspective view of a CT apparatus used to practice the present invention which includes a detector array having rows and columns of detector elements and fan beam source.

Referring now to FIG. 1, a CT scanner for use with the present invention includes a gantry 20 having an opening that defines an imaging area (not separately numbered) where gantry 20 supports an x-ray source 10 oriented to project a fan beam 40 of x-rays along a beam axis 41 through a patient 42 to an opposed detector array 44. The gantry 20 rotates to swing the beam axis 41 within a gantry plane 38 defining the x-y plane of a Cartesian coordinate system. Rotation of gantry 20 is measured by beam angle B from an arbitrary reference position within the gantry plane 38.

A patient 42 resets on a patient support table 46 which may be moved along a translation axis 48 aligned with a Z-axis of the Cartesian coordinate system. Table 46 crosses gantry plane 38 and is radio-translucent so as not to interfere with the imaging process.

The x-rays of the fan beam 40 diverge from the beam axis 41 within the gantry plane 38 across a transverse axis 50 generally orthogonal to both the beam axis 41 and the translation axis 48 at a fan beam angle γ. The x-rays of beam 40 also diverge slightly from the beam axis 41 and the gantry plane 38 across the translation axis 48 (i.e., along the Z axis).

After passing through patient 42, the x-rays of the fan beam 40 are received by detector array 44 which has detector elements 18' arranged in eight rows extending along the traverse axis 50 and a plurality of columns extending along the translation axis 48. The surface of detector array 44 may be planar or may follow a section of a sphere or cylinder having a center at focal spot 26 or alternatively at the system isocenter.

The detector elements 18' each receive x-rays and provide intensity measurements along separate rays of the fan beam 40. Each intensity measurement describes the attenuation via a line integral of one fan beam ray passing through a portion of volume or region of interest (ROI) 43 of patient 42. ROI 43 is typically wider along the Z-axis than the slice volume measured by a conventional CT system fan beam along the Z-axis. The rows of detector elements 18' subdivide the detector array and hence the fan beam along the Z-axis.

Figure 2:
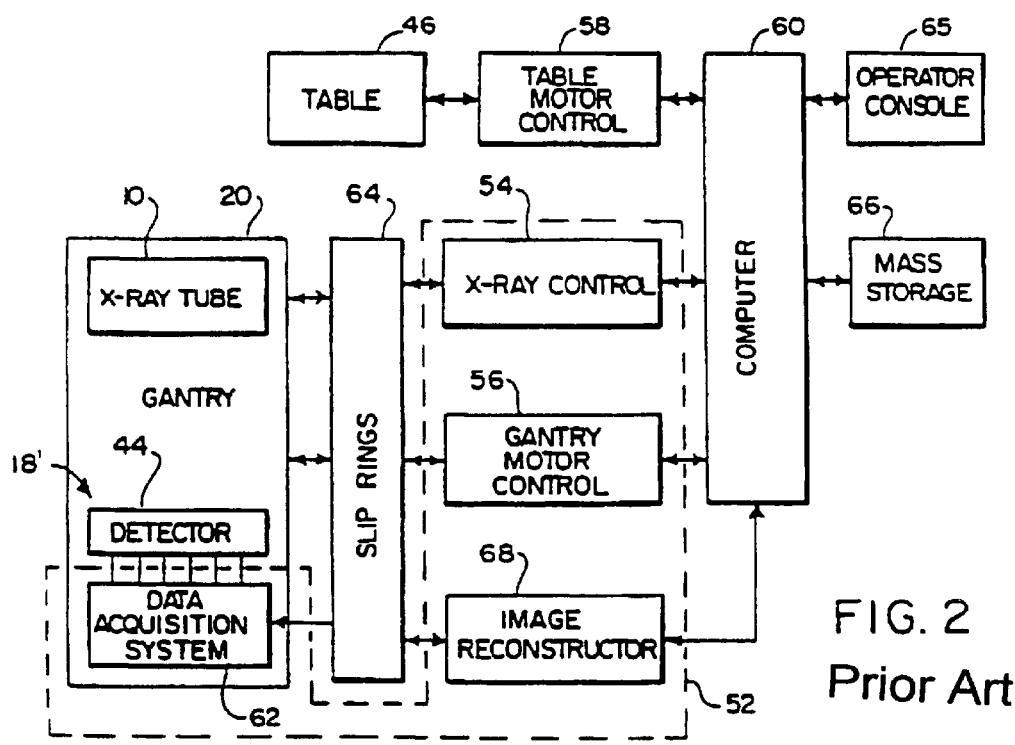
FIG. 2 is a block diagram of CT control system which may be used to control the CT apparatus of FIG. 1 and which is useful for the purposes of practicing the present invention.

Referring now to FIG. 2, an exemplary control system for controlling the CT imaging system of FIG. 1 includes a plurality of gantry associated control modules 52, a table motor control 58, a computer 60, an operator's console 65 and a mass storage device 66. The gantry associated control modules 52 include an x-ray control module 54, a gantry motor control module 56, a data acquisition system 62 and an image reconstructor 68. The x-ray control 54 provides power and timing signals to the x-ray source 10 to turn the source on and off as required under the control of computer 60. The gantry motor control 56 controls the rotational speed and position of the gantry 20 and provides information to computer 60 regarding gantry position. The table motor control 58 controls translation speed of table 46 and provides position feedback information back to computer 60.

Data acquisition system 62 samples and digitizes intensity signals from the detector elements 18' of detector array 44 and provides the digitized signals to computer 60 which in turn stores the signals in mass storage device 66. A slip ring connects all gantry mounted elements to other system components that are not mounted to the gantry for two way communication as well known in the art. After data is collected, image reconstructor 52 is controlled to combine the collected data to form images for display via console 65 or some other display device.

Referring still to FIGS. 1 and 2, computer 60 runs a pulse sequencing program to perform the inventive data processing method as described in more detail below. To this end, computer 60 receives commands and scanning parameters via operator console 65 which is generally a CRT display and keyboard. Console 65 allows an operator to enter parameters for controlling a data acquiring scan, to select images to be displayed and to display reconstructed image and other information from computer 60. A mass storage device or memory 66 provides a means for storing operating programs for the CT imaging system, as well as image data for future reference by the operator. Both computer 60 and image reconstructor 52 have associated electronic memory (not shown) for storing data.

In operation, gantry motor control 56 brings gantry 20 up to a rotational speed and table motor control 58 begins translation of the table 46. The x-ray control 54 turns on the x-ray source 10 and projection data is acquired on the continuous basis as the table is moved through, and the gantry 20 is rotated about, the imaging area. At each beam angle B, the projection data acquired comprises intensity signals corresponding to each detector element 18' at each particular column and row of array 44. After data acquisition, the data is stored as helical data in mass storage device 66 and can be weighted and filtered to generate slice image data corresponding to separate trans-axial slice images through the ROI 43 using any of various processes as well known in the art.

B. Assumptions

Figure 4:
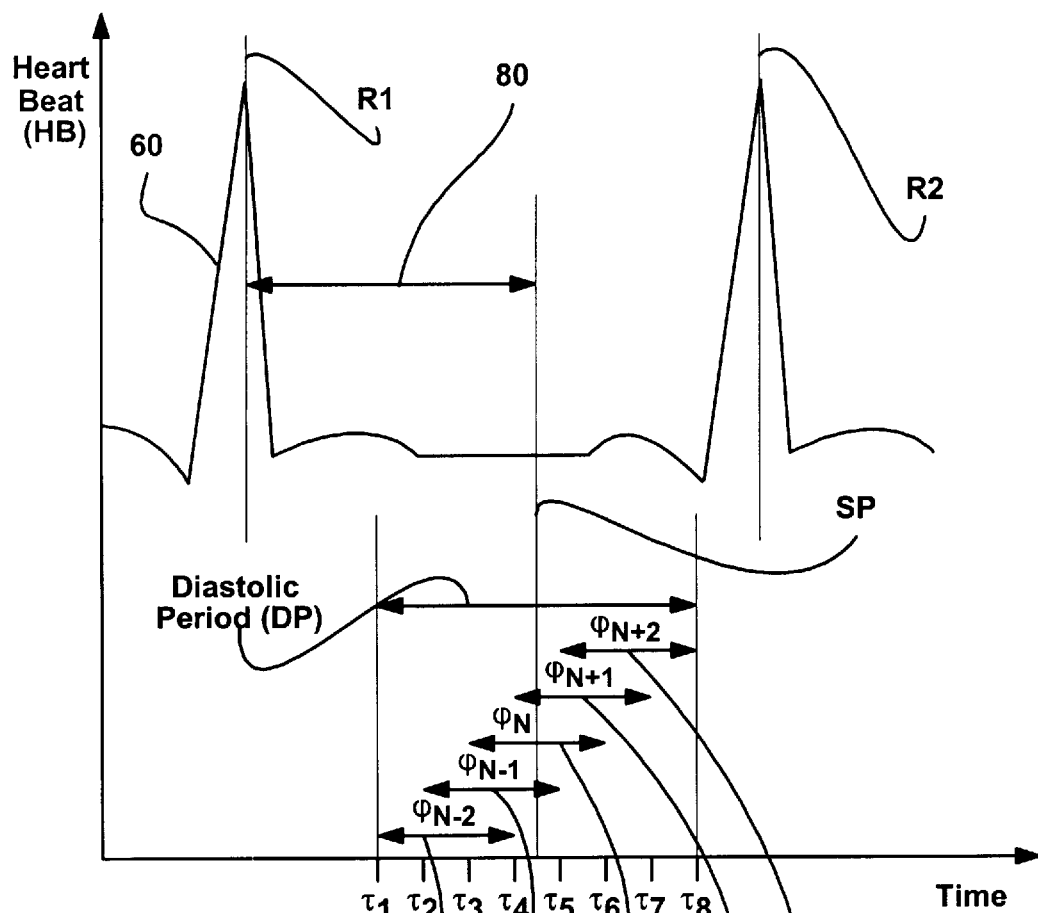
FIG. 4 is a graph and schematic diagram illustrating an exemplary heart beaing cycle, an exemplary diastolic phase and phase ranges corresponding to the diastolic phase and also image sets corresponding to each of the phase ranges.
Figure 4:
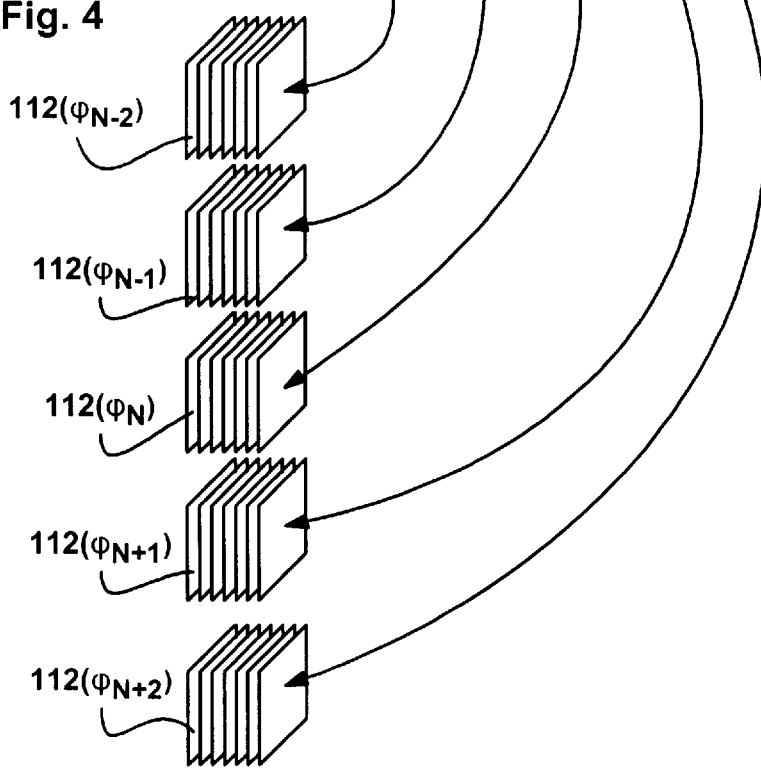

Referring now to FIGS. 1 and 4, for the purposes of this explanation, it will be assumed that ROI 43 includes patient 42's heart characterized by a heart beating waveform 60 that has a typical cycle period P between peak amplitude points R1 and R2 and that has a diastolic phase DP that generally occurs between heart beating phase times $\tau_1$ and $\tau_8$. In addition, it will be assumed that helically acquired data is stored in its raw helical format initially and is only converted to slice image data after a system operator selects a heart beat phase at which to view an image of the heart.

In addition, while the invention is applicable to either retrospective or prospective gating systems, the invention will be described herein in the context of a prospective shoot and move gating system where a processor controls data acquisition so that acquisition is only acquired during diastolic periods.

Figure 3:
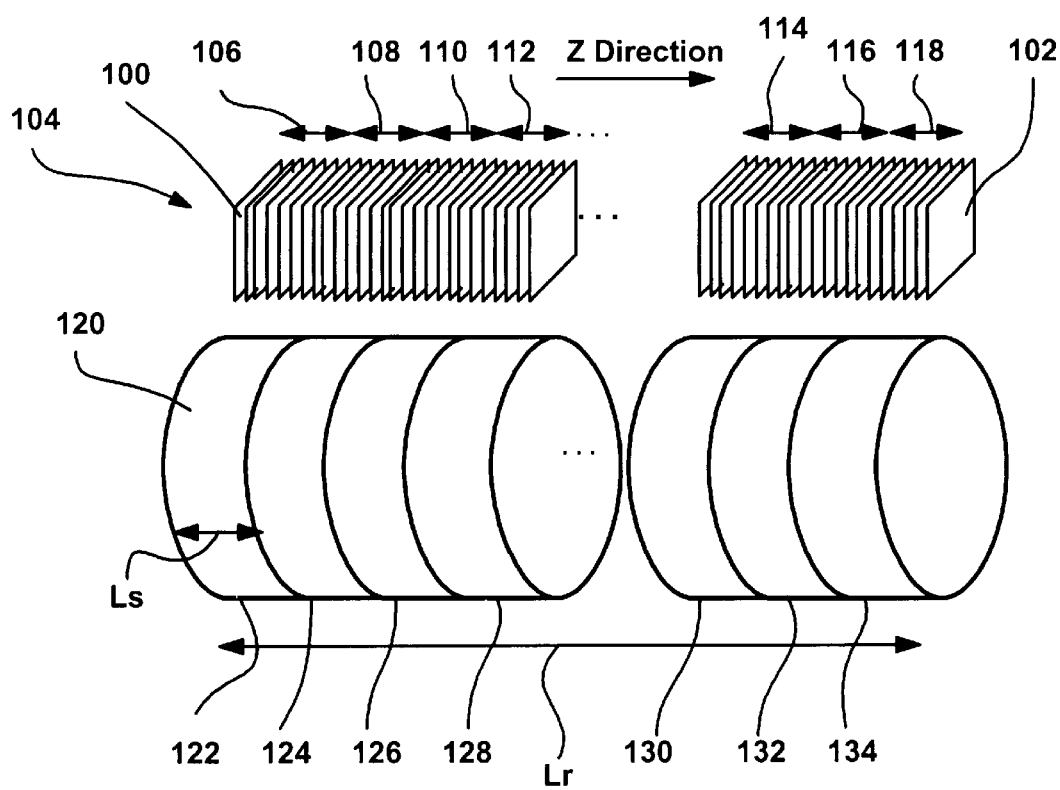
FIG. 3 is a schematic diagram illustrating a region of interest subdivided into sub-volumes and a two-dimensional image stack corresponding thereto.

Moreover, referring also to FIG. 3, it will be assumed that ROI 43 has a dimension Lr along the Z-axis 48 and that a typical helical scanning rate only enables collection of data corresponding to a z-axis dimension Ls during a diastolic acquisition phase DP where dimension Ls is one tenth of the dimension Lr. Thus, ROI 43 is dividable into ten separate sub-volumes 122, 124, 126, 128 . . . 130, 132 and 134 (only seven shown), a separate sub-volume corresponding to each diastolic phase.

Furthermore, unless indicated otherwise, it will be assumed that a system operator requests that the system generate a total of 70 equi-spaced transaxial slice images through ROI 43. To this end, in FIG. 3, an exemplary slice image stack is identified by numeral 104 with separate stack end images identified by numerals 100 and 102. Thus, with ten separate sub-volumes and a required 70 equi-spaced slice images, seven separate images correspond to each sub-volume. In FIG. 3 the separate image sets corresponding to sub-volumes 122, 124, 126, 128, 130, 132 and 134 are identified by numerals 106, 108, 110, 112, 114, 116 and 118, respectively. In FIG. 4, the diastole acquisition phase DP illustrated corresponds to sub-volume 128 and image set 112 generally.

In addition, it will be assumed that, while the diastolic phase ranges from times $t_1$ through $t_8$ (see FIG. 4), enough data is collected during a shorter phase range to generate the images within a sub-volume image set. For instance, referring again to FIGS. 3 and 4, during a phase range $\psi_N$ between times $t_3$ and $t_6$ data sufficient to generate slice images in set 112 is acquired.

C. Theory

Figure 5:
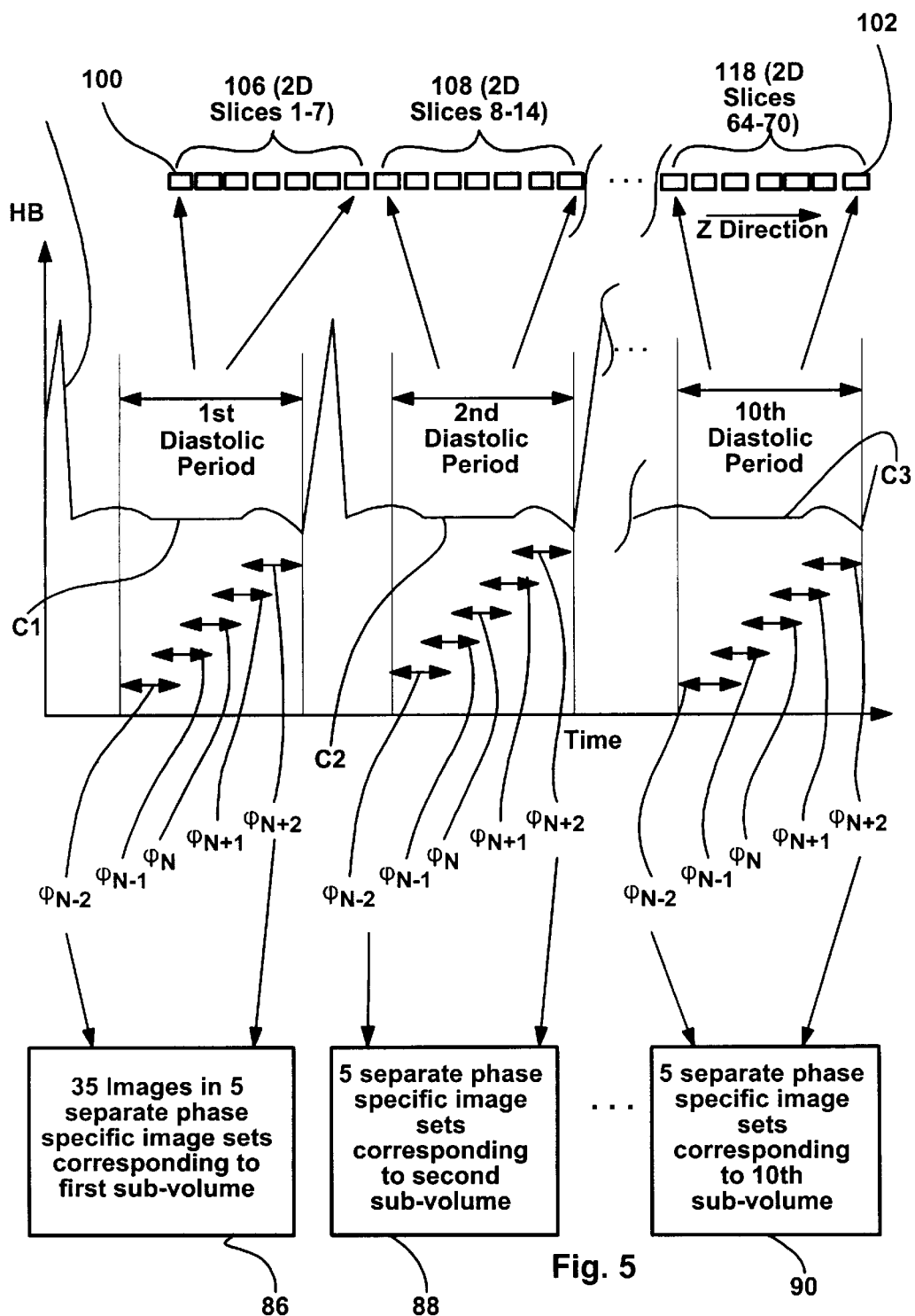
FIG. 5 is similar to FIG. 4 albeit illustrating a series of diastolic phases and corresponding image sets.

Referring now to FIG. 5, a plurality of sequential heart beating cycles C1, C2, . . . C10, like the cycle in FIG. 4 are illustrated, where each cycle includes a separate diastolic phase DP1, DP2, . . . DP10, respectively. In addition, referring to FIGS. 3 and 5, separate image sets 106, 108 . . . 118 corresponding to sub-volumes 122, 124 . . . 134 are also illustrated. Consistent with prior EKG gating techniques, during each diastolic phase, data corresponding to a separate set of images and a separate sub-volume is collected. For instance, during first phase DP1 data corresponding to transaxial slice image set 106 (i.e., including images 1–7) is collected, during phase DP2 data corresponding to transaxial slice image set 108 (i.e., including images 8–14) is collected and so on.

Referring still to FIG. 4, after the helical data is stored and during a post-acquisition period, when choosing images to be viewed, a system operator selects a specific phase point or location SP from within the diastolic phase DP at which the image reconstructor (see 68 in FIG. 1) should create the 70 required transaxial slice images. Thereafter, reconstructor 68 retrieves a sub-set of image data corresponding to phase ranges centered on the phase location SP within each diastolic phase and uses the data sub-sets to generate the 70 required images. For instance, in FIG. 4, with selected phase location SP as illustrated, reconstructor 68 selects the data sub-set corresponding to phase range $\psi_N$ to generate slice image set 106($\psi_N$). Similarly, referring to FIG. 5, reconstructor 68 selects the data sub-set corresponding to phase range $\psi_N$ within diastolic phase DP2 to generate a slice image set 108($\psi_N$) (not separately illustrated), selects the data sub-set corresponding to phase range $\psi_N$ within diastolic phase DP10 to generate a slice image set 118($\psi_N$) (not separately illustrated) and so on. Thereafter reconstructor 68 employs any of several different well known processes to generate slice images corresponding to the separate selected data sub-sets.

Figure 6:
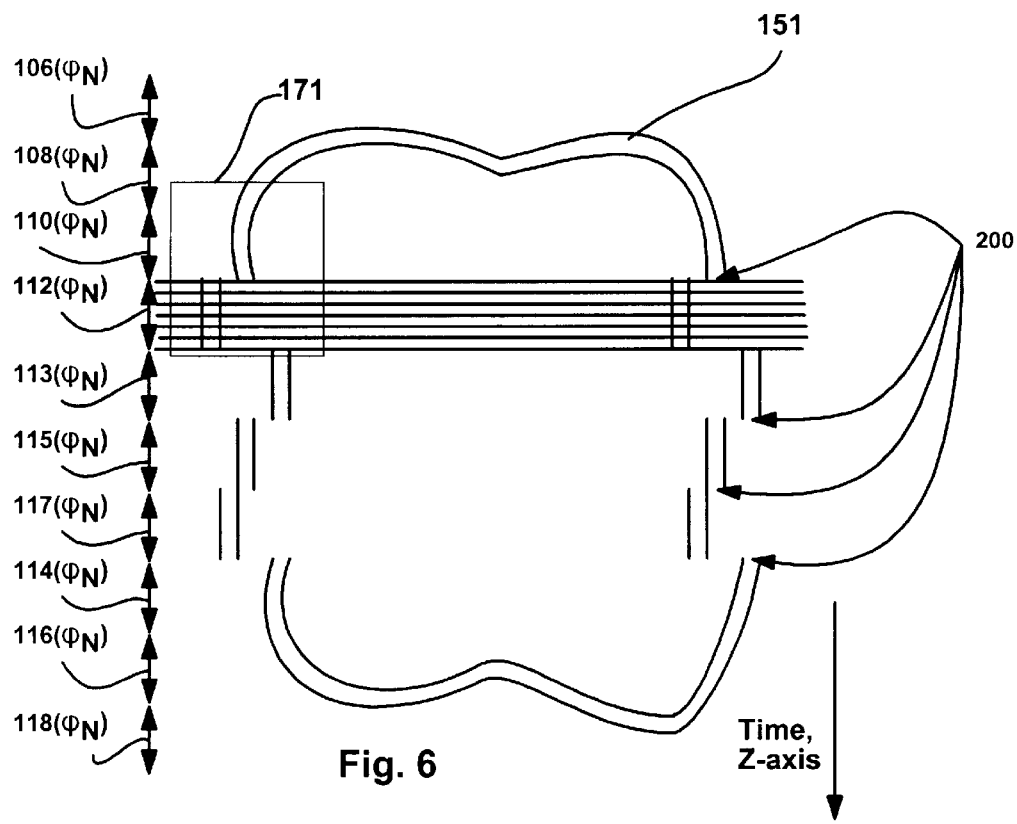
FIG. 6 is a schematic diagram illustrating two-dimensional images in coronal view which correspond to different diastolic phases and generally the same phase range within each of the diastolic phases.

Referring now to FIGS. 1 and 6, a schematic illustrates exemplary image sets within the X-Y transaxial plane that may be generated by reconstructor 68 in the manner described above using data corresponding to phase ranges $\psi_N$. Consistent with the description above, image sets are identified by numerals 106$\psi_N$, 108$\psi_N$, etc., with each set corresponding to a separate ROI sub-volume (e.g., 122, 124, etc. in FIG. 3). While seven separate slice images correspond to each image set, separate images are only illustrated for image set 112 ($\psi_N$).

In FIG. 6, the outline of an anatomical structure 151 (e.g., the left ventricle wall of patient 42's heart) is captured by the image sets. It can be seen that some adjacent image sets are aligned such that the structure outline 151 appears continuous between adjacent image sets. For instance, as illustrated, image set 106$\psi_N$ appears to be aligned with image sets 108$\psi_N$ and 110$\psi_N$ and image set 116$\psi_N$ appears to be aligned with image sets 114$\psi_N$ and 108$\psi_N$. However, because of structure movement and other system operating nuances, structure outline segments corresponding to other adjacent image sets are misaligned or misregistered. For instance, one misregistration occurs between image sets 110$\psi_N$ and 112$\psi_N$. Other misregistrations are illustrated in FIG. 6 and the misregistrations are collectively identified by numeral 200.

When the slice images illustrated in FIG. 6 are further manipulated to generate sagital or coronal images or even thick axial images that combine slice images from different sub-volumes, the misregistrations 200 cause artifacts that reduce diagnostic value appreciably.

It has been recognized that, in many cases, image sets corresponding to different phase ranges within sequential diastolic phases align better than image sets corresponding to the same phase ranges within sequential diastolic phases. To this end, referring to FIG. 4, diastolic acquisition period DP may be sub-divided into separate phase ranges $\psi_{N-2}$, $\psi_{N-1}$, $\psi_N$, $\psi_{N+1}$ and $\psi_{N+2}$ where the duration of each phase range corresponds to sufficient helical data to generate a corresponding slice image set. For instance, data to generate seven image slice data set $112(\psi_{N+2})$ corresponds to phase range $\psi_{N+2}$, data to generate seven image slice data set $112(\psi_{N+1})$ corresponds to phase range $\psi_{N+1}$, data to generate seven image slice data set $112(\psi_{N-1})$ corresponds to phase range $\psi_{N-1}$ and data to generate seven image slice data set $112(\psi_{N-2})$ corresponds to phase range $\psi_{N-2}$. Thus, in the present example, 35 separate images arranged in five separate phase dependent sets $112(\psi_{N-2})$, $112(\psi_{N-1})$, $112(\psi_N)$ $112(\psi_{N+1})$ and $112(\psi_{N+2})$ can be generated during diastolic phase DP where each set corresponds to the same sub-volume (e.g., 128 in the present example as illustrated in FIG. 3).

Figure 7:
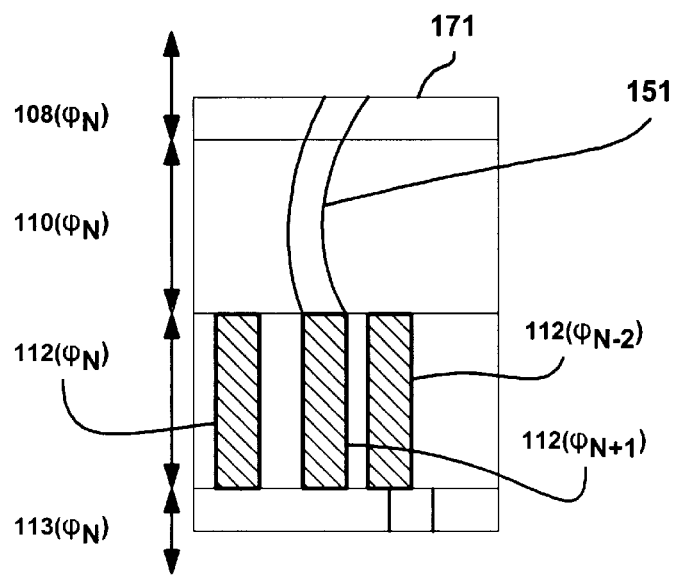
FIG. 7 is a schematic diagram illustrating a portion of the diagram in FIG. 6.

Referring also to FIG. 7, a schematic corresponding to section 171 of FIG. 6 is illustrated and includes the left portions of structure outline 151 that correspond to image sets $110\psi_N$ and $112\psi_N$ and segments of the structure outline corresponding to image sets $108\psi_N$ and $113\psi_N$. In addition, section 171 also illustrates the left portions of structure outline 151 that correspond to image sets $112(\psi_{N+1})$ and $112(\psi_{N-2})$ (the left portions of outline 151 corresponding to image sets $112(\psi_{N+2})$ and $112(\psi_{N-1})$ are not illustrated in FIG. 7). Clearly image set $112(\psi_{N-2})$ registers (i.e., is aligned) more closely with adjacent image set $110(\psi_N)$ than does image set $112(\psi_N)$ and therefore misregistration between the image sets generally can be reduced if, assuming that image set $110(\psi_N)$ is included in a working image set, image set $112(\psi_{N-2})$ is substituted for image set 112 $(\psi_N)$.

Similarly, image set $112(\psi_{N+1})$ registers (i.e., is aligned) precisely with adjacent image set $110(\psi_N)$ and therefore misregistration between the image sets generally can be reduced if, again assuming image set $110(\psi_N)$ is included in a working image set, image set $112(\psi_{N+1})$ is substituted for image set $112(\psi_N)$.

Thus, by generating a plurality of phase range dependent image sets for each diastolic phase and then identifying best aligned image sets, an optimal working image set can be generated that has better diagnostic characteristics. In the present example, referring again to FIG. 4, during each diastolic phase DP1, DP2, etc., the period is divided into five separate phase ranges $\psi_{N-2}$, $\psi_{N-1}$, $\psi_N$, $\psi_{N+1}$ and $\psi_{N+2}$ and the helical phase range dependent image data is then used to generate five separate image sets where each set includes seven separate images. Thereafter, the image sets corresponding to adjacent ROI sub-volumes (see again 128–134 in FIG. 3) are compared to identify an optimal working set including a separate image set corresponding to each sub-volume where the optimal set may include image sets from different phase ranges.

D. Operation

Figure 8:
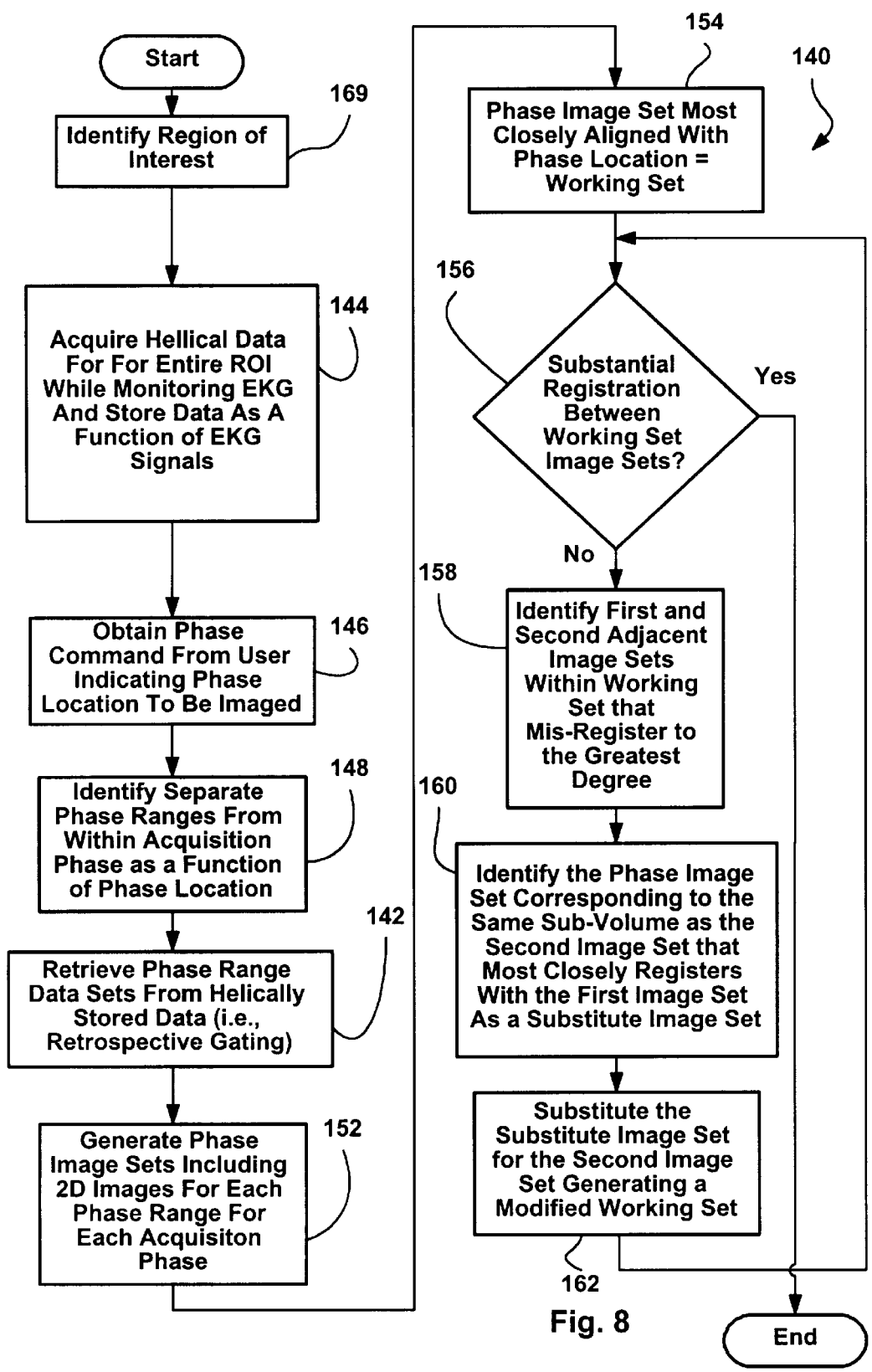
FIG. 8 is a flow chart illustrating a method according to the present invention.

Referring now to FIG. 8, a retrospective gating method 140 according to the present invention is illustrated. Referring also to FIGS. 1, 2 and 3, at process block 169, a system operator uses operator console 65 to identify a ROI 43 within patient 42 through which 70 transaxial two-dimensional slice images 104 should be generated.

At block 144, during data acquisition, the imaging system 38 collects helical CT image data for the entire ROI 43 and stores the helical data as a function of EKG signals (i.e., as a function of acquisition cycles) within mass storage device 66.

After all of the helical data has been acquired for ROI 43 and stored in storage device 66, control passes to block 146 where a system operator used console 65 to identify a phase command that indicates a particular phase location to be imaged. To this end, referring again to FIG. 4, the exemplary selected phase location is identified as SP. Continuing, at block 148, computer 60 identifies separate phase ranges from within each diastolic phase as a function of the phase location SP. In the present example, referring still to FIG. 4 and also to FIG. 5, computer 60 sub-divides each diastolic phase into five separate phase ranges where a central range $\psi_N$ is centered on selected location SP and is between times $\tau_3$ and $\tau_6$ two leading phase ranges and two following phase ranges that lead and follow the centered phase range $\psi_N$, respectively. The leading phase ranges include a phase range $\phi_{N-2}$ ranging between times $\tau_1$ through $\tau_4$ and phase range $\psi_{N-1}$ that extends between times $\tau_2$ and $\tau_5$. The following phase ranges include phase range $\psi_{N+1}$ ranging between times $\tau_4$ through $\tau_7$ and phase range $\phi_{N+1}$ that occurs between times $\tau_5$ and $\tau_8$. Thus, in the present example, the phase ranges overlap somewhat.

Continuing, at block 142, computer 60 retrieves data from device 66 corresponding to each of the phase ranges and for each of the diastolic phases (i.e., retrospective gating function) and at block 152 computer 60 causes image reconstructor 68 to generate phase image sets including 2D images for each phase range for each diastolic period. For instance, referring once again to FIG. 4, image reconstructor 68 generates a separate image set including seven images for each of phase period $\psi_{N-2}$, $\psi_{N-1}$, $\psi_N$, $\psi_{N+1}$ and $\psi_{N+2}$ for sub-volume 128 (see also FIG. 3) where sub-volume 128 corresponds to one of the diastolic phases. Similarly, referring also to FIG. 5, five separate phase specific image sets are generated for each of the other sub-volumes 122, 124, 126, . . . 130, 132 and 134 where each of these sub-volumes corresponds to a separate one of the diastolic phases. All of the image sets are stored within mass storage device 66.

Continuing, and again referring to FIGS. 2, 4, 5 and 6, computer 60 selects the phase image sets that are most closely aligned with the selected phase location SP and generates a working image set including all of the selected phase image sets. In the present example, the phase image set most closely aligned with location SP correspond to phase range $\psi_N$ and, as described above are illustrated in FIG. 6. This step occurs at block 154. At block 156, computer 60 compares all of the working set image sets (see again FIG. 6) to determine whether or not substantial registration between the working set image sets exists. Where substantial registration does exist, control passes out of the process and the process ends. However, at block 156, where substantial registration between the working set image sets does not exist, control passes to block 158 where computer 60 identifies first and second adjacent image sets within the working set that are misregistered to the greatest degrees. For instance, in the present example, computer 60 may identify working set image sets $110(\psi_N)$ and $112(\psi_N)$ as the most misaligned or misregistered adjacent image sets. Herein it will be assumed that image set $110(\psi_N)$ and image set $112(\psi_N)$ are identified as the first and second sets, respectively.

Continuing, at block 160 computer 60 identifies the phase image set corresponding to the same diastolic phase as the second image set that most closely registers with the first image set as a substitute image set. Referring once again to FIG. 8, in the present example, computer 60 identifies phase image set $112(\psi_{N+1})$ as the image set corresponding to the second phase image set 112 $(\psi_N)$ that is most closely aligned with the first image set $110(\psi_N)$. At block 162, computer 60 substitutes the substitute image set for the second image set generating a modified working set. Thereafter, control again passes back up to block 156 where computer 60 continues to determine whether or not the working set image sets are substantially registered and, where they are not substantially registered, continues to substitute other phase images sets until substantial or optimal registration results.

It should be understood that the methods and apparatuses described above are only exemplary and do not limit the scope of the invention, and that various modifications could be made by those skilled in the art that would fall under the scope of the invention.

For example, there are many different image comparison algorithms that measure the degree of misregistration in the prior art that could be used to perform the image set comparisons and the present invention is not limited to any one such process.

As another example, while the present invention as described above is one wherein raw helical data is stored and image sets are only generated after a system operator selects a location SP (see again FIG. 4) for image processing, it should be appreciated that other embodiments exist where, for example, phase dependent two-dimensional image sets may be generated for each diastolic phase and the phase dependent image sets may be stored prior to selection of location SP. In this case, after a location SP is selected, computer 60 may simply access the phase image sets for each diastolic phase and select the image sets from each diastolic phase that are most closely aligned with location SP. Thereafter, the process described in FIG. 8 including blocks 156, 158, 160 and 162 could be performed as described above.

In addition, while the inter-diastolic phase ranges are shown above as overlapping, the present invention may be performed with truly sequential phase ranges where adjacent phase ranges do not overlap or, in the alternative, may be performed with phase ranges that are separated by some small range. Moreover, while the invention is particularly useful for image purposes during diastolic phases, clearly, other phases such as the systolic phases may be targeted for image processing according to the present invention. In fact, because the systolic phases is generally shorter than the diastolic phase the present invention may be particularly advantageous for imaging during the systolic phase. Furthermore, while the invention as described above in the context of EKG gated applications, clearly the present invention is useful other applications where periodic structural motion occurs.

To apprise the public of the scope of this invention, the following claims are made:

1. A method to be used with a CT imaging system for minimizing phase misregistration among the two dimensional CT images that make up a working image set corresponding to a region of interest (ROI), the method comprising the steps of:

identifying separate sequential acquisition phases during an acquisition period;

obtaining helical data corresponding to the separate acquisition phase;

for each acquisition phase:
(i) identifying at least two different phase ranges; and
(ii) generating and storing images as phase image sets corresponding to the different phase ranges;

comparing the phase image sets corresponding to sequential ranges to identify substantially aligned phase image sets; and selecting the substantially aligned phase image sets as the working image set for the ROI.

2. The method of claim 1 wherein the step of identifying acquisition phases includes the step of monitoring the cycle of a cyclical anatomical function and wherein the step of obtaining includes gating helical data acquisition so as to coincide with the cycles of the anatomical function.

3. The method of claim 2 wherein the anatomical function is a heart beating cycle and each acquisition phase corresponds to at least one heart cycle phase.

4. The method of claim 3 wherein the at least one heart cycle phase is the diastolic phase.

5. The method of claim 3 wherein the at least one heart cycle phase is the systolic phase.

6. The method of claim 1 wherein the step of obtaining includes the steps of acquiring a full set of helical data while monitoring the cycle of a cyclical anatomical function and storing the helical data as a function of the cyclical anatomical data, the step of identifying acquisition phases includes, after the helical data is stored, identifying a separate phase of the anatomical function cycle and the step of obtaining further includes the step of retrieving the helical data corresponding to the separate acquisition phase.

7. The method of claim 6 wherein the anatomical function is a heart beating cycle and each acquisition phase corresponds to at least one heart cycle phase.

8. The method of claim 1 further including the step of, prior to comparing, identifying a specific phase point from within an acquisition period and wherein the step of comparing includes selecting phase image sets most closely corresponding to the identified phase point as a working set and comparing the working set image sets to identify misalignment and wherein the step of selecting includes substituting non-working set image sets for working set image sets where the substitutions reduce misalignment and provide a modified working image set.

9. The method of claim 8 wherein the step of comparing the working set images includes the steps of:
(a) identifying working set image sets corresponding to sequential acquisition phases that have the greatest degree of misalignment as first and second image sets;
(b) identifying a non-working set image set corresponding to the same acquisition phase as the second image set as a substitute image set;
(c) substituting the substitute image set for the second image set; and
(d) repeating steps (a) through (c) until a substantially aligned working image set results.

10. The method of claim 9 wherein the step of identifying a non-working set image set includes the step of identifying a non-working set image set corresponding to the same acquisition phase as the second image set that is most aligned with the first image set as the substitute image set.

11. The method of claim 1 wherein the phase ranges overlap.

12. The method of claim 1 wherein the phase ranges are consecutive.

13. The method of claim 1 wherein the step of identifying at least two phase ranges includes the step of identifying more than two phase ranges for each acquisition phase.

14. The apparatus of claim 1 wherein the program causes the processor to perform the step of obtaining by acquiring a full set of helical data while monitoring the cycle of a cyclical anatomical function and storing the helical data as a function of the cyclical anatomical data, the program causes the processor to perform the step of identifying acquisition phases by, after the helical data is stored, identifying a separate phase of the anatomical function cycle and wherein the the step of obtaining further includes retrieving the helical data corresponding to the separate acquisition phase.

15. An apparatus to be used with a CT imaging system for minimizing phase misregistration among the two dimensional CT images that make up a working image set corresponding to a region of interest (ROI), the apparatus comprising:
 a processor running a pulse sequencing program to perform the steps of:
  identifying separate sequential acquisition phases during an acquisition period;
  obtaining helical data corresponding to the separate acquisition phase;
  for each acquisition phase:
   (i) identifying at least two different phase ranges; and
   (ii) generating and storing images as phase image sets corresponding to the different phase ranges;
  comparing the phase image sets corresponding to sequential ranges to identify substantially aligned phase image sets; and
  selecting the substantially aligned phase image sets as the working image set for the ROI.

16. The apparatus of claim 15 wherein the program causes the processor to perform the step of identifying acquisition phases by monitoring the cycle of a cyclical anatomical function and wherein the step of obtaining includes gating helical data acquisition so as to coincide with the cycles of the anatomical function.

17. The apparatus of claim 16 wherein the anatomical function is a heart beating cycle and each acquisition phase corresponds to at least one heart cycle phase.

18. The apparatus of claim 15 wherein the program further causes the processor to, prior to comparing, identify a specific phase point from within an acquisition period and wherein the program causes the processor to perform the step of comparing by acquisition phases by selecting phase image sets most closely corresponding to the identified phase point as a working set and comparing the working set image sets to identify misalignment and wherein the program causes the processor to perform the step of selecting by substituting non-working set image sets for working set image sets where the substitutions reduce misalignment and provide a modified working image set.

19. The apparatus of claim 15 wherein the phase ranges overlap.

20. The apparatus of claim 15 wherein the phase ranges are consecutive.

21. The apparatus of claim 15 wherein the step of identifying at least two phase ranges includes the step of identifying more than two phase ranges for each acquisition phase.

* * * * *